United States Patent
Takeda et al.

(10) Patent No.: US 8,221,481 B2
(45) Date of Patent: Jul. 17, 2012

(54) BRAIN COOLING DEVICE AND BRAIN COOLING SYSTEM COMPRISING THE DEVICE

(75) Inventors: Yoshimasa Takeda, Okayama (JP); Kiyoshi Morita, Okayama (JP); Kouji Yoshida, Izumi (JP); Takeharu Kobayashi, Izumi (JP)

(73) Assignees: National University Corporation Okayama University (JP); Daiken Iki Kabushiki Kaisha (JP)

( * ) Notice: Subject to any disclaimer, the term of this patent is extended or adjusted under 35 U.S.C. 154(b) by 1147 days.

(21) Appl. No.: 11/992,045

(22) PCT Filed: Sep. 13, 2006

(86) PCT No.: PCT/JP2006/318171
§ 371 (c)(1),
(2), (4) Date: Mar. 14, 2008

(87) PCT Pub. No.: WO2007/032397
PCT Pub. Date: Mar. 22, 2007

(65) Prior Publication Data
US 2009/0177258 A1    Jul. 9, 2009

(30) Foreign Application Priority Data
Sep. 16, 2005    (JP) ................... 2005-270359

(51) Int. Cl.
*A61F 7/00*    (2006.01)
(52) U.S. Cl. ....................................... 607/105

(58) Field of Classification Search ............ 607/104, 607/105, 113, 116, 124, 126; 606/192, 194; 128/207.14–207.15
See application file for complete search history.

(56) References Cited

U.S. PATENT DOCUMENTS

| | | | | |
|---|---|---|---|---|
| 5,865,176 A | * | 2/1999 | O'Neil | ............ 128/207.15 |
| 2005/0222652 A1 | | 10/2005 | Mori | |
| 2008/0275535 A1 | | 11/2008 | Mori | |

FOREIGN PATENT DOCUMENTS

| | | |
|---|---|---|
| EP | 0 922 465 | 6/1999 |
| JP | 11-206885 | 8/1999 |
| JP | 2000-060890 | 2/2000 |
| JP | 2000-245764 | 9/2000 |
| JP | 2000-325388 | 11/2000 |
| WO | WO 2005/097016 | 10/2005 |

* cited by examiner

*Primary Examiner* — Nicholas Lucchesi
*Assistant Examiner* — Melissa A Snyder
(74) *Attorney, Agent, or Firm* — Gerald E. Hespos; Michael J. Porco

(57) ABSTRACT

A brain cooling device is provided to cool the brain sufficiently to the subcortical tissue in a short time. The device includes a cuff (3) capable of storing therein a cooled fluid and placeable in the esophagus (H1) of the patient (H) when inserted orally or transnasally. A tube (2) extends from the cuff (3) for infusing the fluid into the cuff (3) placed in the esophagus (H1) from outside the body of the patient H and discharging the fluid from the cuff (3). The cuff (3) has flexibility so as to inflate or deflate in response to infusion or discharge of the fluid and is configured in such a manner that when the fluid is infused therein while placed in the esophagus (H1), the cuff (3) that has been inflated comes into close contact with the inner wall (H4) of the esophagus (H1).

8 Claims, 13 Drawing Sheets

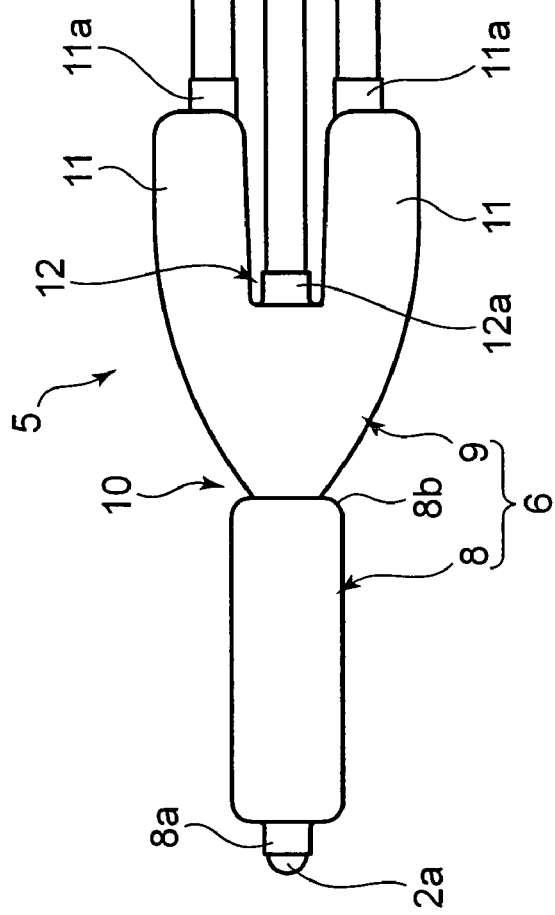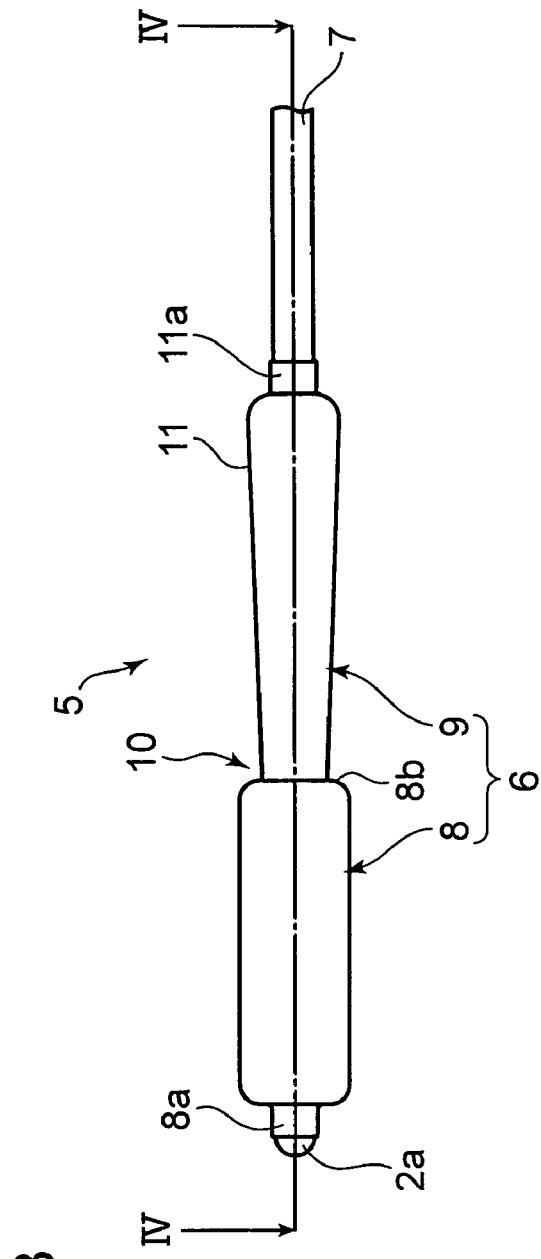
FIG.3A
FIG.3B

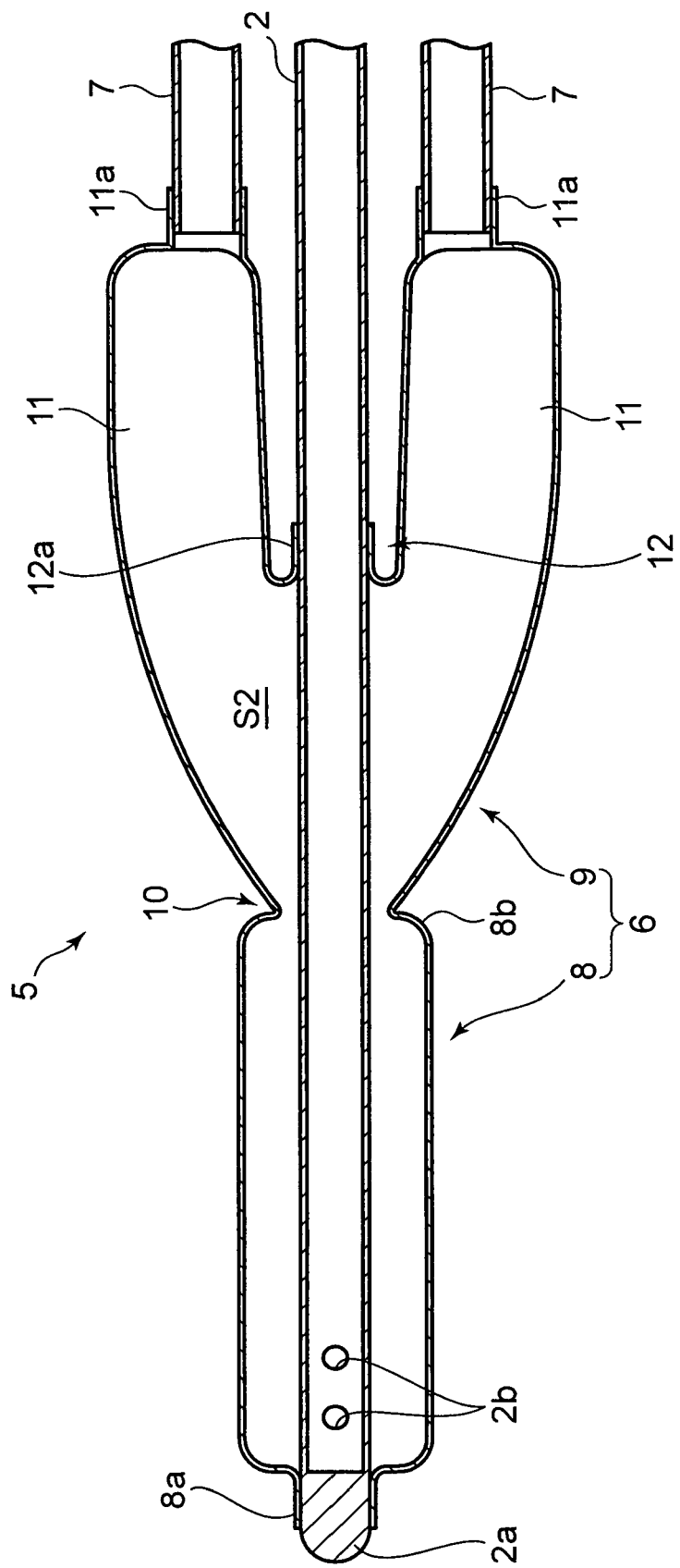

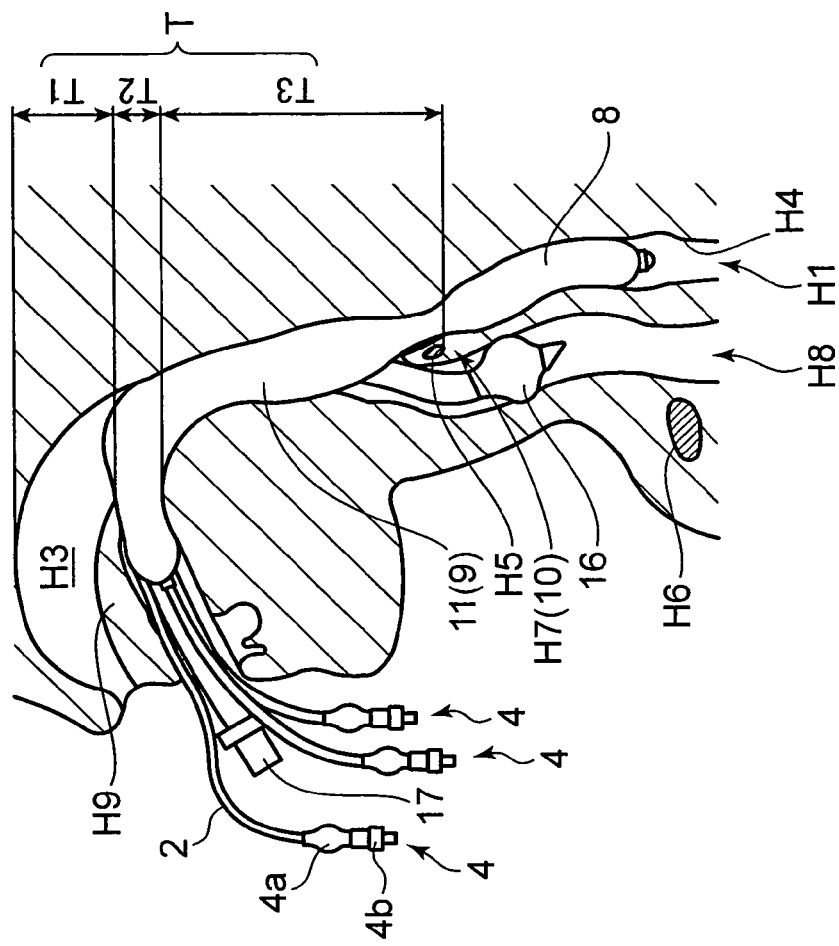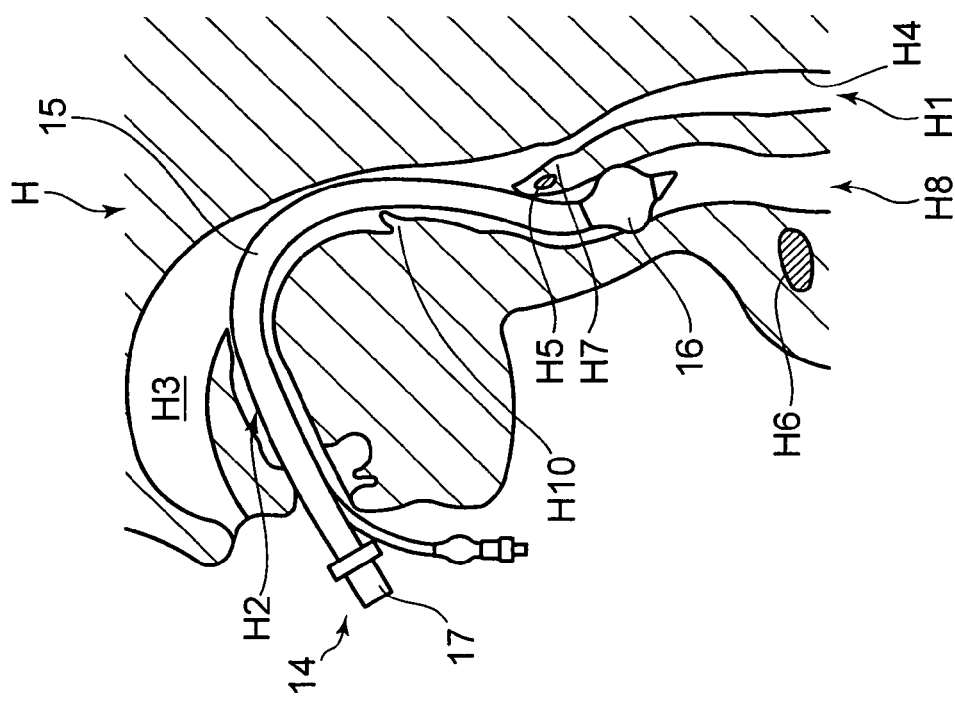

BRAIN COOLING DEVICE AND BRAIN COOLING SYSTEM COMPRISING THE DEVICE

BACKGROUND OF THE INVENTION

1. Field of the Invention

The present invention relates to a brain cooling device.

2. Description of the Related Art

In organisms such as a human body, an amount of oxygen supplied to the brain becomes insufficient due to a failure of the respiratory function or the circulatory function like in a cardiac arrest (hereinafter, referred to as the cardiac arrest state), and this insufficient oxygen supply is known to cause a death of brain cells, so-called ischemic neuron damage.

Meanwhile, treatment for resuscitation from the cardiac arrest state, such as artificial respiration, is practiced on an organism in the cardiac arrest state. However, even in a case where the organism in the cardiac arrest state is resuscitated by this treatment, aftereffects are highly likely to occur in the brain due to the ischemic neuron damage.

Under these circumstances, a treatment to cool the brain by lowering the body temperature of an organism in the cardiac arrest state with the aim of suppressing the occurrence of the ischemic neuron damage, known as the hypothermic treatment, has been proposed in recent years.

The hypothermic treatment is more effective when it is practiced sooner upon the occurrence of ischemia, and the treatment effect decreases sharply with an elapse of time.

Adopted in the hypothermic treatment are a method for lowering the body temperature of an organism by wrapping the whole body with a blanket or the like inside of which a cooling fluid is circulating, and a method for directly cooling the head by covering the head of the organism with a covering material inside of which a cooling fluid is circulating as is disclosed, for example, in JP-A-2000-60890.

In each case where the body temperature is lowered using the blanket or the covering material, however, the body is cooled from the surface of the body. Hence, not only it takes a time to lower the temperature of the brain, but also it is difficult to cool the brain sufficiently to the subcortical tissue.

In a case where the organism is resuscitated from the cardiac arrest state while the whole body is cooled with the blanket, there is a risk of inducing irregular heartbeats accompanying a drop in temperature of the whole body. Accordingly, careful attention should be paid to the cooling timing of the organism with the use of this blanket.

SUMMARY OF THE INVENTION

The invention was devised in view of the problems discussed above, and has an object to provide a brain cooling device capable of cooling the brain sufficiently to the subcortical tissue in a short time and a brain cooling system including this device.

In order to solve the problems discussed above, the invention provides a brain cooling device, characterized by including: a first storage portion capable of storing therein a cooled fluid and placeable in an esophagus of an organism when inserted orally or transnasally; a second storage portion to be placed at a pharyngeal region of the organism while the first storage portion is placed in the esophagus of the organism and capable of storing therein the cooled fluid; and infusion and discharge means provided so as to extend from the first and second storage portions for fusing the fluid into the first and second storage portions placed in the organism from outside a body of the organism and discharging the fluid from the first and second storage portions, wherein the first and second storage portions have flexibility to inflate or deflate in response to infusion or discharge of the fluid and are configured in such a manner that when the fluid is infused therein while placed in the organism, the first storage portion that has been inflated comes into close contact with an inner wall of the esophagus and the second storage portion that has been inflated comes into close contact with the pharyngeal region.

According to the invention, by infusing the fluid into the storage portion placed in the esophagus, the storage portion can be brought into close contact with the inner wall of the esophagus. It is thus possible to cool the inner wall of the esophagus with the cooled fluid inside the storage portion. Because the blood vessels (carotid arteries) that supply blood to the brain are concentrated in the vicinity of the esophagus, cooling these blood vessels with the storage portion makes it possible to cool the brain by cooling the blood flowing in these blood vessels.

As has been described, according to the invention, not only can the brain be cooled in a short time because the blood vessels in a relatively close distance from the brain are cooled from inside the body (esophagus), but also the brain can be cooled sufficiently to the subcortical tissue because the brain is cooled via the blood.

Also, according to the invention, because the brain is cooled by cooling the inner wall of the esophagus alone, in comparison with a case where the whole body is cooled, it is possible to suppress a drop in temperature of the whole body, which can reduce concerns about the cooling timing.

Further, according to the invention, by infusing the fluid into the second storage portion placed at the pharyngeal region (a region closer to the mouth or the nose than to the esophagus: indicated by a capital T in FIG. 5B), the second storage portion can be brought into close contact with the pharyngeal region. It is thus possible to cool the pharyngeal region with the cooled fluid inside the second storage portion. Also, as with the esophagus, because blood vessels (carotid arteries) that supply blood to the brain are concentrated in the vicinity of the pharyngeal region, too, cooling these blood vessels with the second storage portion makes it possible to cool the brain by cooling the blood flowing in these blood vessels.

Hence, according to this configuration, combined with the cooling of the inner wall of the esophagus, it is possible to cool the brain more effectively.

In addition, the invention provides a brain cooling system, including the brain cooling device described above, and an airway maintaining member capable of maintaining an airway of the organism when inserted orally or transnasally, to which the brain cooling device is attached.

According to the brain cooling system of the invention, because the airway of the organism can be maintained with the airway maintaining member, it is possible to concurrently practice the cardiac arrest resuscitation treatment, such as artificial respiration, and the hypothermic treatment by cooling the brain.

The phrase, "to which the brain cooling device is attached", means not only that the brain cooling device and the airway maintaining member are combined into a single unit, but also that these components are removable. To be more specific, in a case where the brain cooling system is inserted into the organism orally or transnasally, the airway maintaining member may be inserted into the organism orally or transnasally before insertion of the brain cooling device for introducing the brain cooling device into the esophagus along the airway maintaining member.

Meanwhile, in a case where the brain cooling device and the airway maintaining member are combined into a single unit, an operation to insert the both components into the organism can be carried out at a time, which can enhance the workability.

BRIEF DESCRIPTION OF THE DRAWINGS

FIG. 1 shows a shape of the tip end of a brain cooling device according to a first embodiment of the invention.

FIG. 3 shows a shape of the tip end of a cooling device according to a second embodiment of the invention, and FIG. 3A is a plan view and FIG. 3B is a side view.

FIG. 4 is a cross section taken on line IV-IV of FIG. 3B.

FIG. 5 is a sectional side view showing the procedure to insert the cooling device of FIG. 3 into the patient, and FIG. 5A shows a state where an endotracheal tube is inserted into the patient and FIG. 5B shows a state where the cooling device is inserted into the patient.

FIG. 7 shows the enlarged tip end of the brain cooling system of FIG. 6.

DETAILED DESCRIPTION OF THE PREFERRED EMBODIMENTS

Hereinafter, preferred embodiments of the invention will be described with reference to the drawings.

Figure 1A:
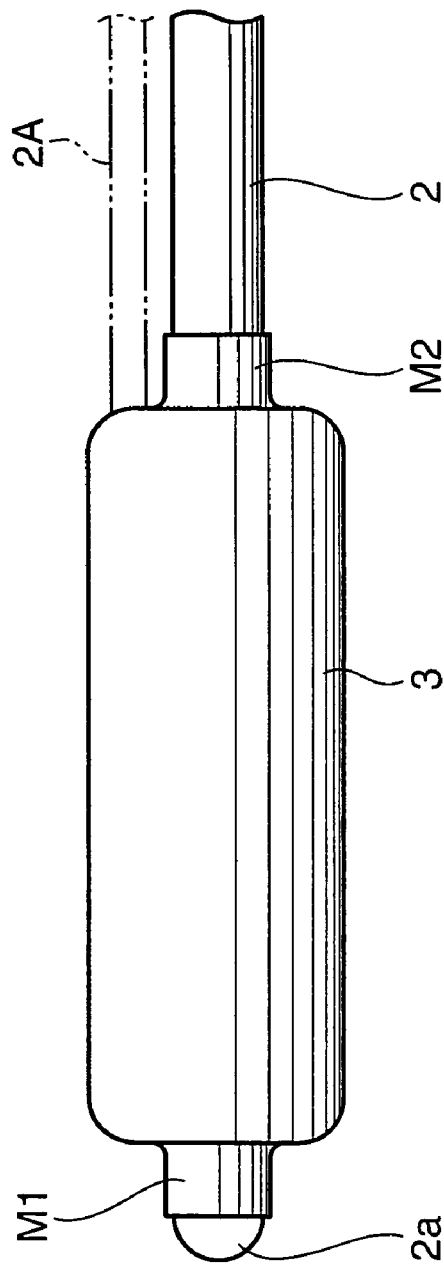
FIG. 1A is a side view and FIG. 1B is a sectional side view.
Figure 1B:
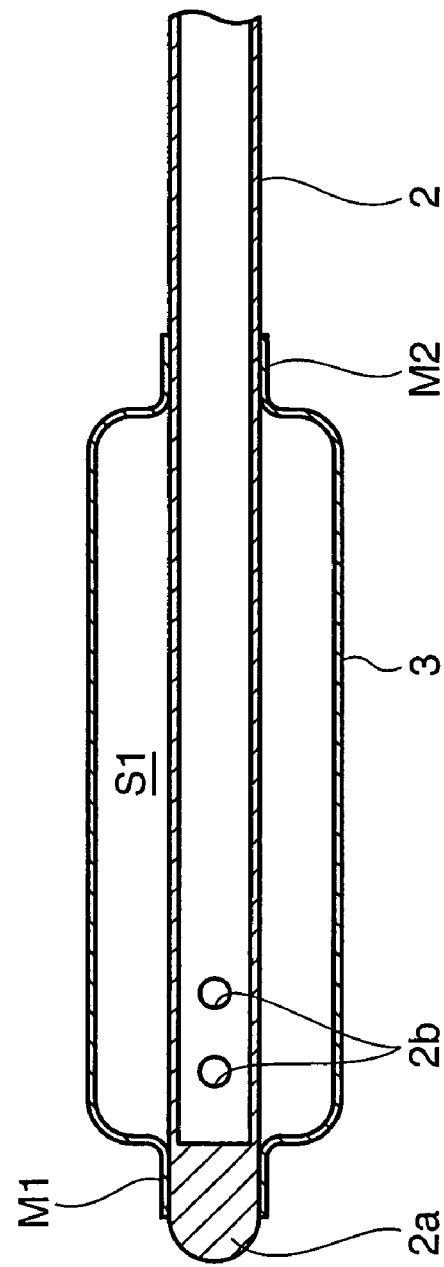
Figure 2:
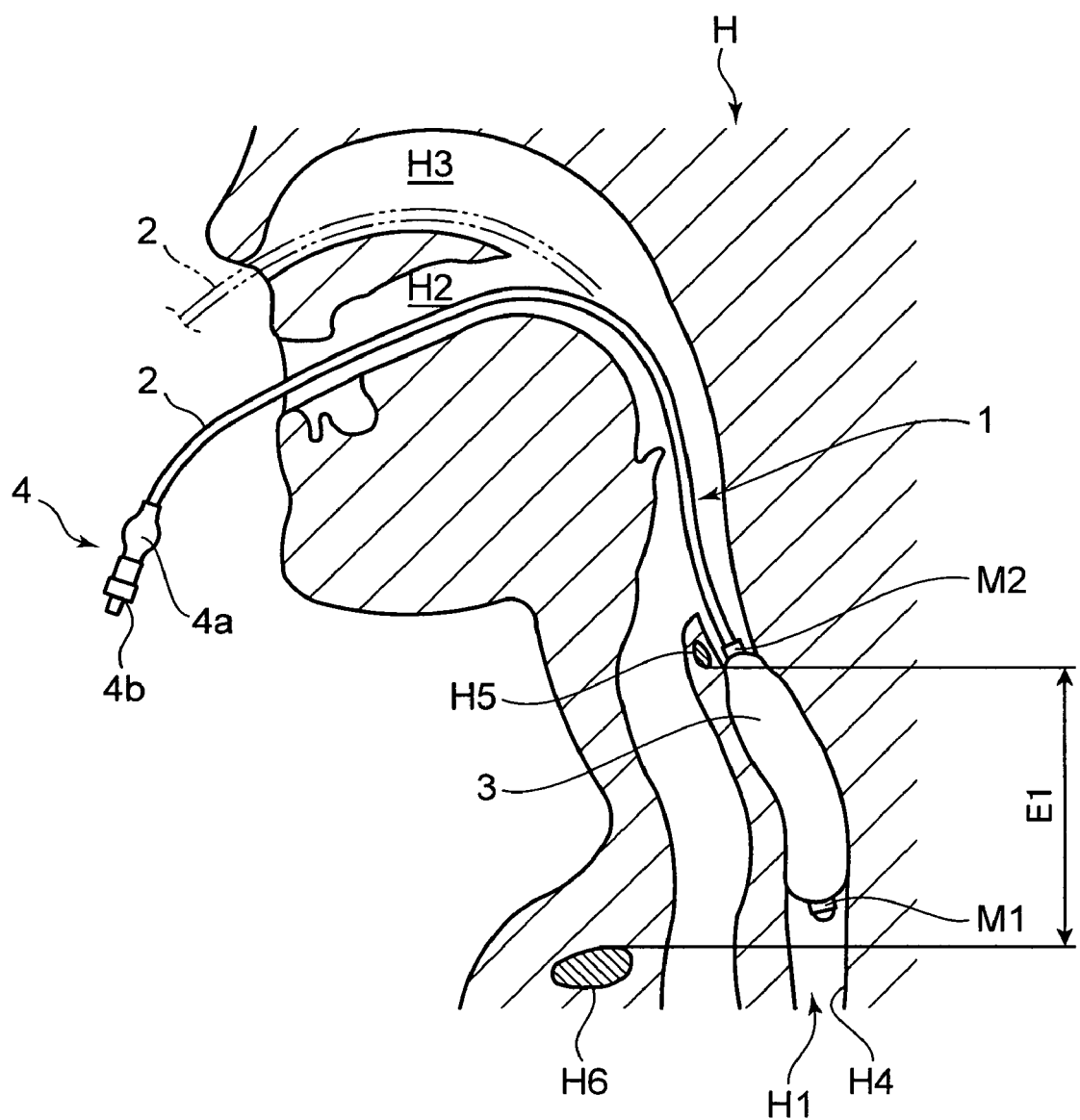
FIG. 2 is a sectional side view showing a state where the brain cooling device of FIG. 1 is inserted into a patient.

FIG. 1 shows a shape of the tip end of a brain cooling device according to a first embodiment of the invention. FIG. 1A is a side view and FIG. 1B is a sectional side view. FIG. 2 is a sectional side view showing a state where the brain cooling device of FIG. 1 is inserted into a patient.

Referring to the respective drawings, a brain cooling device (hereinafter, referred to as the cooling device) 1 includes a tube (infusion and discharge means) 2, a cuff (storage portion) 3 provided to one end of the tube 2, and a port 4 provided to the other end on the opposite side of the cuff 3. Hereinafter, the tube 2 will be described on the assumption that the side provided with the cuff 3 is the tip end and the side provided with the port 4 is the base end.

The tube 2 is a tubular member made of synthetic resin, such as polyamide and polyvinyl chloride. Also, the tube 2 is closed by a bottom portion 2a at the tip end and is provided with plural side holes 2b (two side holes are illustrated in FIG. 1B) penetrating through the side surface at the positions in the vicinity of the bottom portion 2a.

The tube 2 has a length long enough for the base end thereof to reach the outside of the body of the patient H when the cuff 3 described below is placed in the esophagus H1 of the patient H (for example, 18 to 28 cm for adults and 10 to 20 cm for children).

The cuff 3 is made of a material having flexibility, such as silicone resin, and formed in the shape of a bag to be capable of storing therein a cooled fluid. When a fluid is infused therein from the port 4 via the tube 2, it is allowed to inflate outwardly in the radial direction of the tube 2 and deflate inwardly in the radial direction of the tube 2 when the fluid stored therein is discharged by the port 4.

To be more concrete, the cuff 3 is formed by externally attaching a member formed in a circular cylindrical shape to the tube 2 so as to cover the respective side holes 2b and then joining the both ends thereof to the outer peripheral surface of the tube 2 along the entire circumference at joint positions M1 and M2 on the tip end side and the base end side of the side holes 2b, respectively. A storage chamber S1 is thus defined between the tube 2 and the cuff 3 inside the cuff 3 formed in the shape of a bag in this manner.

The port 4 communicates with the base end opening of the tube 2, and is capable of introducing a fluid into the storage chamber S1 via the interior of the tube 2. To be more concrete, the port 4 includes a pilot balloon 4a coupled to the tube 2 and a check valve 4b coupled to the pilot balloon 4a.

The pilot balloon 4a is configured in such a manner that it swells in response to the internal pressure of the cuff 3 while the cuff 3 is in an inflated state. Medical staff is thus able to detect the internal pressure of the cuff 3 by checking the swelling condition by touch with hand.

The check valve 4b has a valve body inside, and because it is of a known configuration to open the valve body when a glass syringe or the like is inserted and closing the valve body when the glass syringe or the like is pulled out, detailed description thereof are omitted herein.

Hereinafter, a method of use of the cooling device 1 will be described.

Initially, the cuff 3 is brought into a deflated state, and the tip end of the tube 2 is inserted into the body of the patient H via the mouth cavity H2 or the nasal cavity H3. The cuff 3 is then introduced into the esophagus H1 through an operation to push in the tube 2 from the outside of the body of the patient H.

In this embodiment, it should be noted that the tube 2 is made of a material, such as polyamide and polyvinyl chloride, whereas the cuff 3 is made of silicone resin, so that the tube 2 has larger rigidity than the cuff 3 due to a difference of characteristics between these materials. It is thus possible to introduce the cuff 3 to the esophagus H1 by an operation to push in the tube 2 from outside the body of the patient H. The rigidity is not necessarily adjusted by the material characteristics as described above. For example, it is possible to provide the larger rigidity to the tube 2 than to the cuff 3 by making the tube 2 thicker than the cuff 3.

Further, in this embodiment, because the cuff 3 is penetrated through by the tube 2 having the larger rigidity from the tip end to the base end, it is possible to suppress the bending of the cuff 3 itself.

Subsequently, by an operation to push in the tube 2 further, the cuff 3 fully up to the base end is introduced into the esophagus H1 (the cuff 3 is introduced to the depth position of FIG. 2).

A pre-cooled cooling agent (a fluid having a high specific heat: for example, fat emulsion) is infused into the cuff 3 from the port 4 while it is placed in the esophagus H1. Accordingly, the cuff 3 inflates and comes into close contact with the inner wall H4 of the esophagus H1. Accordingly, the inner wall H4 of the esophagus H1 is cooled by drawing heat from the inner wall H4 with the cooling agent.

When a specific cooling time has elapsed, the cuff 3 is pulled out from the patient H by pulling out the tube 2 after the cuff 3 is deflated by discharging the cooling agent from the port 4.

As has been described, according to the cooling device 1, by infusing the cooling agent into the cuff 3 placed in the esophagus H1, the cuff 3 can be brought into close contact with the inner wall H4 of the esophagus H1. It is thus possible to cool the inner wall H4 of the esophagus H1 with the cooling agent inside the cuff 3. Because blood vessels (carotid arteries) that supply blood to the brain are concentrated in the vicinity of the esophagus H1, cooling these blood vessels with the cuff 3 makes it possible to cool the brain by cooling the blood flowing in these blood vessels.

As has been described, according to the cooling device 1, not only can the brain be cooled in a short time because the blood vessels in a relatively close distance from the brain are cooled from inside the body (esophagus H1), but also the brain can be cooled sufficiently to the subcortical tissue because the brain is cooled via the blood.

Also, according to the cooling device 1, because the brain is cooled by cooling the inner wall H4 of the esophagus H1 alone, in comparison with a case where the whole body is cooled, it is possible to suppress a drop in temperature of the whole body, which can reduce concerns about the cooling timing.

In light of the object of the invention to cool the brain selectively while suppressing a drop in temperature of the whole body by cooling blood vessels in a close distance from the brain, a range to be cooled in the esophagus H1 (the length of the cuff 3) is preferably within a range of the cervical esophagus E1 from the lower edge of the annular cartilage H5 to the upper edge of the clavicle H6 in the esophagus H1 extending from the lower edge of the annular cartilage H5 to the stomach (not shown). When configured in this manner, the inner wall H4 of the esophagus H1 can be cooled at a position relatively spaced apart from the heart. It is thus possible to suppress a drop in temperature of the whole body in a more reliable manner.

In this embodiment, infusion of the cooling agent into the cuff 3 and discharge of the cooling agent from the cuff 3 are carried out using the single tube 2. However, a tube for infusing cooling agent and a tube for discharging cooling agent can be provided separately.

For example, as is shown in FIG. 1A, it may be configured in such a manner that the tube 2 is used to infuse the cooling agent, while a tube 2A coupled to the base end inside the cuff 3 is additionally provided so that the cooling agent stored inside the cuff 3 is discharged from the base end side of the cuff 3 using this tube 2A.

When configured in this manner, the cooling agent that has been stored in the cuff 3 is discharged from the base end side of the cuff 3 via the tube 2A while the cooling agent is being infused into the cuff 3 on the tip end side via the respective side holes 2b in the tube 2.

More specifically, according to the configuration including the tube 2A, because the cooling agent can be discharged from the upper side (the base end side) of the cuff 3 placed in the esophagus H1 of the patient H while the cooling agent is infused from the lower side (tip end side) of the cuff 3, it is possible to allow the cooling agent that has absorbed heat of the patient H inside the cuff 3 to flow inside the cuff 3 along a direction of convection, so that the cooling agent having heat is discharged actively from the cuff 3.

Consequently, because the efficiency of heat exchange between the patient H and the cuff 3 can be enhanced, it is possible to cool the brain more effectively.

The cooling device 1 of this embodiment is configured to cool the esophagus H1 alone. However, by cooling the pharyngeal region T (see FIG. 5B) continuing from the esophagus H1 to the mouth cavity H2 and the nasal cavity H3, it is possible to further enhance the brain cooling efficiency.

FIG. 3 shows a shape of the tip end of a cooling device according to a second embodiment of the invention. FIG. 3A is a plan view and FIG. 3B is a side view. FIG. 4 is a cross section taken on line IV-IV of FIG. 3B.

FIG. 5A is a sectional side view showing a state where an endotracheal tube is inserted into the patient to describe the procedure to insert the cooling device of FIG. 3 into a patient. FIG. 5B is a sectional side view showing a state where the cooling device is inserted to describe the procedure to insert the cooling device of FIG. 3 into the patient.

Referring to the respective drawings, a cooling device 5 includes the tube 2, a cuff 6 provided to the tip end of the tube 2, a pair of discharge tubes 7 extending from the base end of the cuff 6, and the port 4 provided to each of the base ends of the tube 2 and the discharge tubes 7.

The cuff 6 is a bag-shaped member made of silicone resin, flexible polyvinyl chloride, or the like. To be more concrete, the cuff 6 includes a bale-shaped portion (storage portion) 8 on the tip end side and a U-shaped (second storage portion) 9 that bifurcates from the bale-shaped portion 8 toward the base end, which are combined into a single unit.

The bale-shaped portion 8 includes a circular cylindrical portion 8a extending toward the tip end, and it is fixed to the tube 2 as the inner surface of the circular cylindrical portion 8a and the outer surface of the tube 2 inserted through the circular cylindrical portion 8a are joined to each other along the entire circumference. In addition, the base end of the bale-shaped portion 8 serves as a shoulder portion 8b headed inward in the radial direction of the tube 2, and the bale-shaped portion 8 is coupled to the U-shaped portion 9 via the shoulder portion 8b.

Meanwhile, the U-shaped portion 9 is of a shape that opens outwardly in the radial direction of the tube 2 while headed toward the base end from the shoulder portion 8b. In other words, at the boundary of the bale-shaped portion 8 and the U-shaped portion 9, a recess portion 10 whose sectional area when the cuff 6 is in the inflated state is made smaller than those of the other portions is formed. The recess portion 10 is formed to correspond to the narrow segment H7 at the boundary of the pharyngeal region T and the esophagus H1 of the patient H.

The U-shaped portion 9 includes a pair of leg portions 11 extending toward the base end and a crotch portion 12 between these leg portions 11, which are combined into a single unit.

The crotch portion 12 includes a circular cylindrical portion 12a extending toward the base end, and it is fixed to the tube 2 as the inner surface of the circular cylindrical portion 12a and the outer surface of the tube 2 inserted through the circular cylindrical portion 12a are joined to each other along the entire circumference.

A circular cylindrical portion 11a extending toward the base end is formed in the base end of each leg portion 11. Each leg portion 11 is fixed to the corresponding discharge tube 7 as the inner surface of the corresponding circular cylindrical portion 11a and the outer surface at the tip end of the corresponding discharge tube 7 inserted through the circular cylindrical portion 11a are joined to each other along the entire circumference.

In short, the cuff 6 defines a storage chamber S2 on the outside of the tube 2 as the circular cylindrical portions 8a, 11a, and 12a are joined to the corresponding tube 2 and discharge tubes 7.

Hereinafter, a method of use of the cooling device 5 will be described.

Initially, as is shown in FIG. 5A, the airway of the patient H is maintained using an endotracheal tube 14. The endotracheal tube 14 includes a tube main body 15 that is orally or transnasally insertable into the patient H. The endotracheal tube 14 is used to block the upper end of the trachea H8 by inflating a cuff 16 attached to the tip end of the tube main body 15 while the tip end of the tube main body 15 is introduced into the trachea H8 of the patient H first, and thence in this state to supply oxygen to the inside of the trachea H8 via the lumen of the tube main body 15 from an artificial respirator (not shown) connected to the connector 17 at the base end of the tube main body 15.

Subsequently, the cuff 6 of the cooling device 5 is deflated and the tip end of the tube 2 is inserted into the body of the patient H via the mouth cavity H2 while the both leg portions 11 of the cuff 6 are placed on the both sides of the tube main body 15 of the endotracheal tube 14. Then, the bale-shaped portion 8 of the cuff 6 is introduced into the esophagus H1 by an operation to push in the tube 2 from outside the body of the patient H while letting the tube 2 pass along the top surface of the tube main body 15 of the endotracheal tube 14.

By an operation to push in the tube 2 further, the cuff 6 is introduced inside until the recess portion 10 is placed at the narrow segment H7 of the patient H as is shown in FIG. 5B.

In this state, the bale-shaped portion 8 of the cuff 6 is placed in the esophagus H1, while at the same time, the U-shaped portion 9 is placed in a region from the hypopharynx T3 to the mouth cavity H2 through the oropharynx T2. Herein, the pharyngeal region T is defined to have three regions: the epipharynx T1 continuing to the nasal cavity H3 above the palate H9, the oropharynx T2 visible when the mouth is open, and the hypopharynx T3 above the annular cartilage H5 at the branching portion of the esophagus H1 and the trachea H8.

Subsequently, the cuff 6 is inflated by infusing the cooling agent therein from the port 4 of the tube 2, so that the bale-shaped portion 8 comes into close contact with the inner wall H4 of the esophagus H1 and the U-shaped portion 9 with the hypopharynx T3 and the oropharynx T2. Accordingly, the inner wall H4 of the esophagus H1 and the pharyngeal region T are cooled by drawing heat from the inner wall H4 and the pharyngeal region T with the cooling agent infused into the cuff 6.

When a specific cooling time has elapsed, the cuff 6 is pulled out from the patient H by pulling out the tube 2 after the cuff 6 is deflated by discharging the cooling agent from the ports 4 of the discharge tubes 7.

As has been described, according to the cooling device 5 of the second embodiment, by infusing the cooling agent into the U-shaped portion 9 placed at the pharyngeal region T, the U-shaped portion 9 can be brought into close contact with the pharyngeal region T (the hypopharynx T3 and the oropharynx T2 in FIG. 5B). It is thus possible to cool the pharyngeal region T with the cooling agent inside the U-shaped portion 9. As with the esophagus H1, blood vessels (carotid arteries) that supply blood to the brain are concentrated in the vicinity of the pharyngeal region T, too, and cooling these blood vessels with the U-shaped portion 9 makes it possible to cool the brain by cooling the blood flowing in these blood vessels.

Hence, according to the cooling device 5, combined with the cooling of the inner wall H4 of the esophagus H1, it is possible to cool the brain more effectively.

FIG. 5A is used to describe the method of use of the cooling device 5 in a case where the endotracheal tube 14 is inserted orally. However, in a case where the endotracheal tube 14 is inserted transnasally, it is also possible to use the cooling device 5 by passing it through the nasal cavity H3 of the patient H. In this case, because the U-shaped portion 9 can be placed also at the epipharynx T1 of the patient H, the brain cooling efficiency can be increased further by cooling the entire pharyngeal region T from the hypopharynx T3 to the epipharynx T1.

In addition, because the cooling device 5 is provided with the recess portion 10 between the bale-shaped portion 8 and the U-shaped portion 9, when the bale-shaped portion 8 and the U-shaped portion 9 are inflated by placing the bale-shaped portion 8 in the esophagus H1 and the U-shaped portion 9 at the pharyngeal region T, it is possible to suppress application of an excessive load on the narrow segment H7 at the boundary of the pharyngeal region T and the esophagus H1 of the patient H.

Further, with the cooling device 5, it is possible to infuse the cooling agent to the tip end side of the bale-shaped portion 8 with the use of the tube 2 while discharging the cooling agent from the base end side of the U-shaped portion 9 with the use of the discharge tubes 7. In other words, the cooling agent can be infused from the lower side of the bale-shaped portion 8 placed in the esophagus H1 of the patient H while discharging the cooling agent from the upper side of the U-shaped portion 9. It is thus possible to allow the cooling agent that has absorbed heat of the organism in the bale-shaped portion 8 and the U-shaped portion 9 to flow along a direction of convection so that the cooling agent having heat is discharged actively.

Hence, according to the cooling device 5, because the efficiency of heat exchange between the patient H and the bale-shaped portion 8 and the U-shaped portion 9 can be enhanced, it is possible cool the brain more effectively by increasing the cooling efficiency of the inner wall H4 of the esophagus H1 and the pharyngeal region T.

The cooling device 5 according to the second embodiment is configured in such a manner that the endotracheal tube 14 to maintain the airway of the patient H and the cooling device 5 are provided separately. However, as are shown in FIG. 6 through FIG. 10, it is possible to combine the cooling device with a component to maintain the airway into a single unit.

Figure 6:
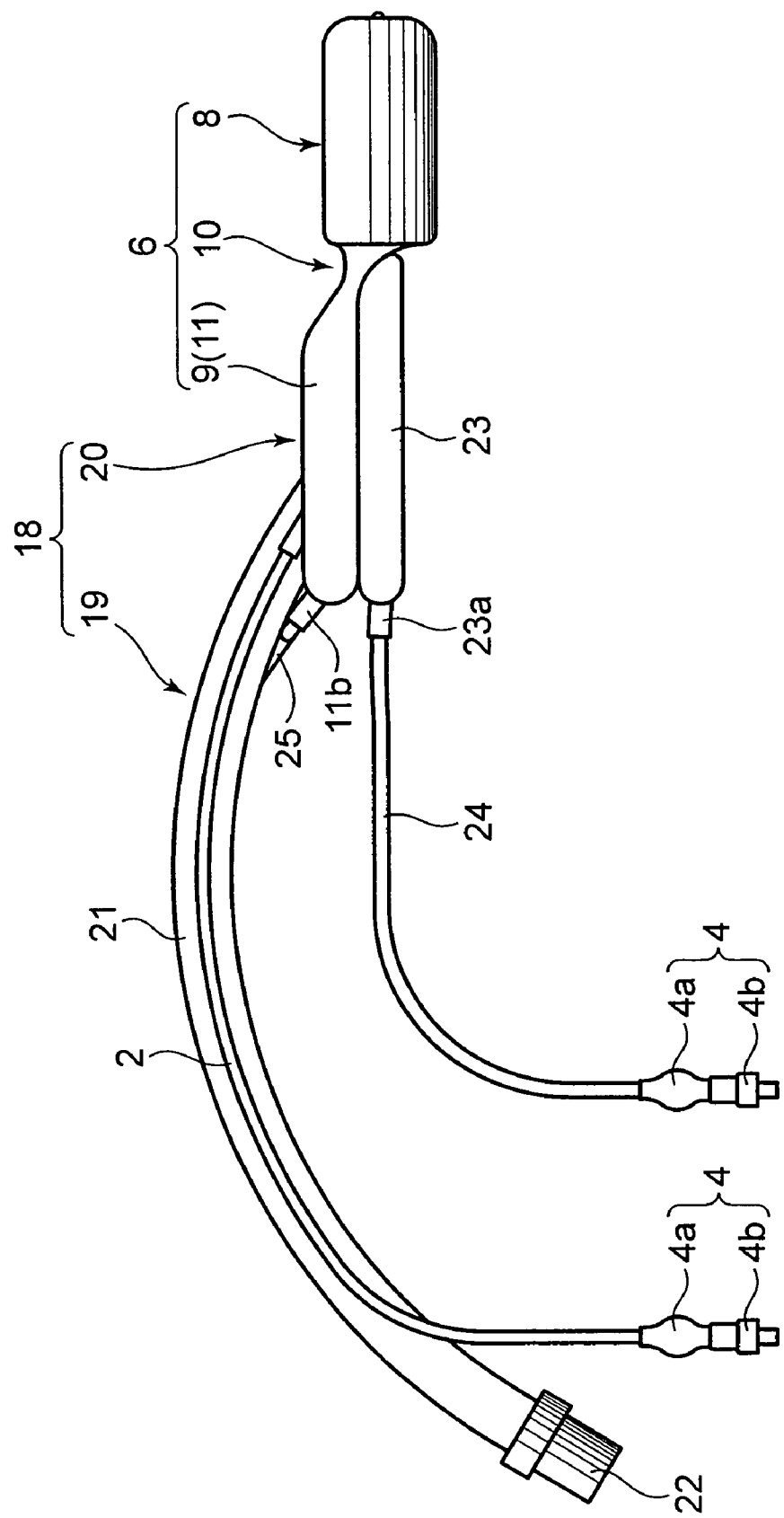
FIG. 6 is a side view showing the overall configuration of a brain cooling system according to a third embodiment of the invention.
Figure 7A:
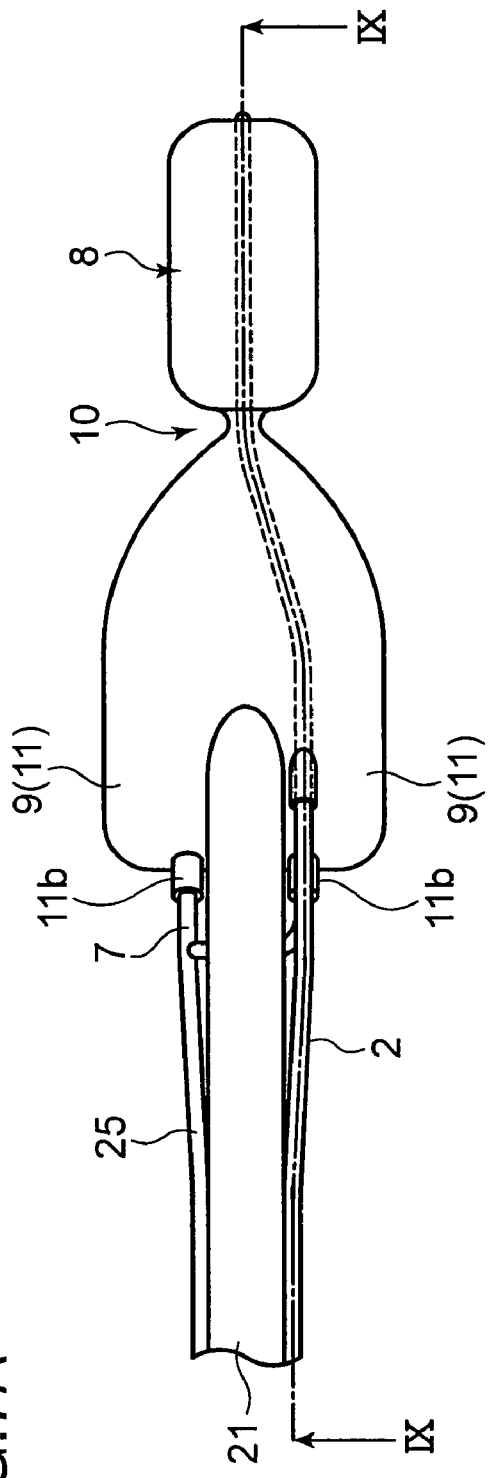
FIG. 7A is a plan view and FIG. 7B is a bottom view.
Figure 7B:
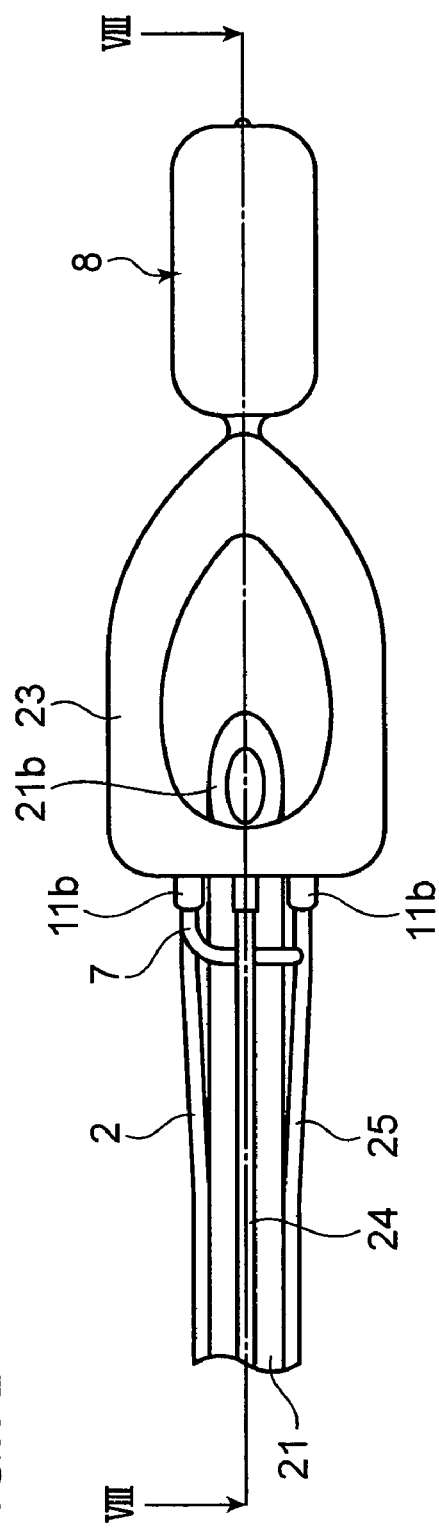
Figure 8:
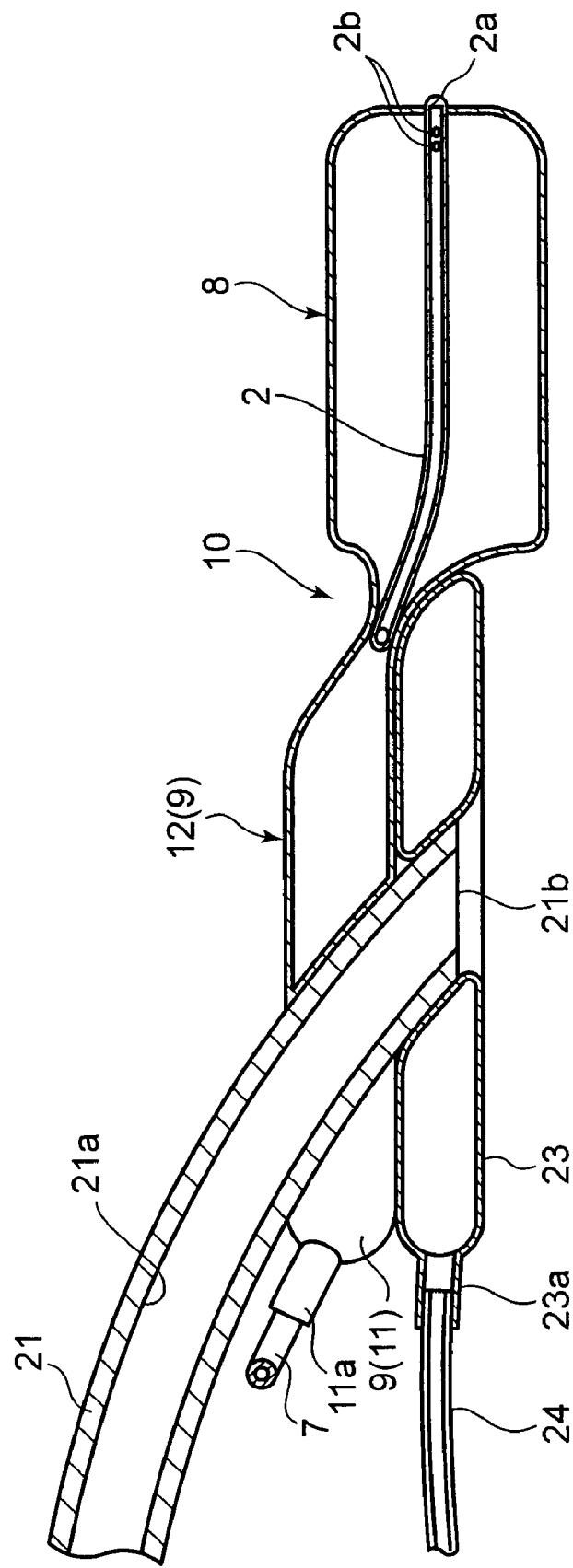
FIG. 8 is a cross section taken on line VIII-VIII of FIG. 7.
Figure 9:
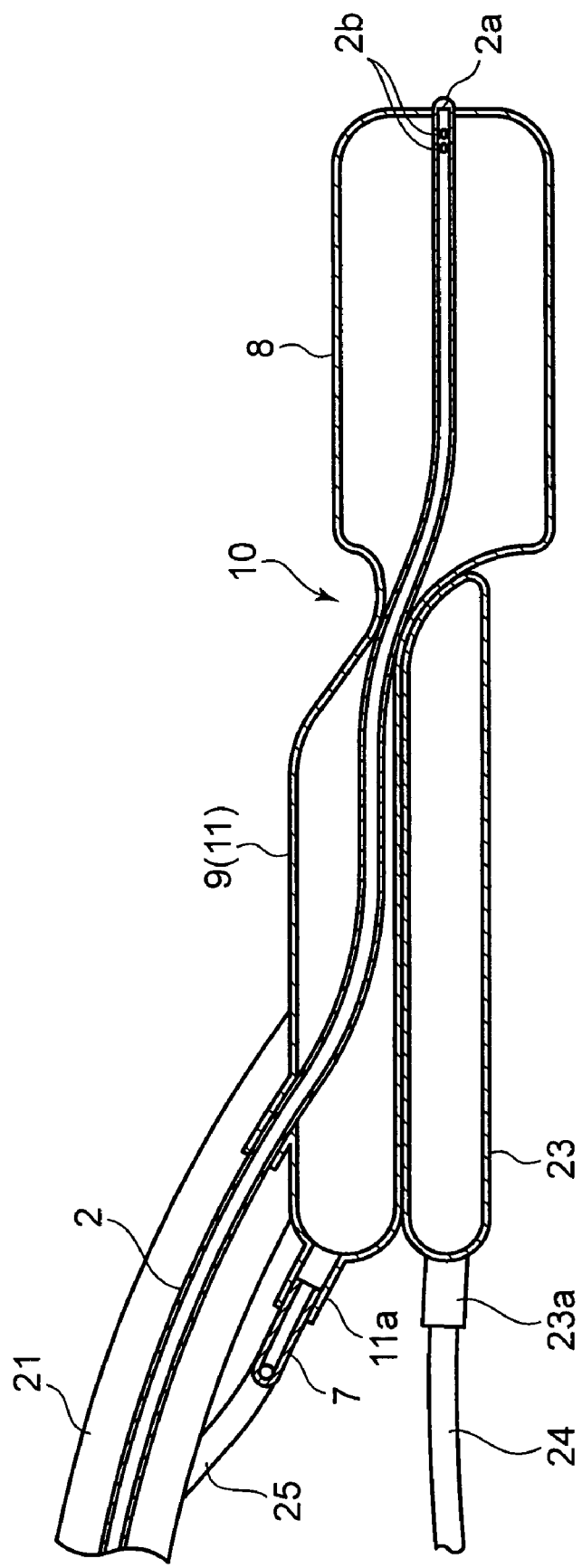
FIG. 9 is a cross section taken on line IX-IX of FIG. 7.
Figure 10:
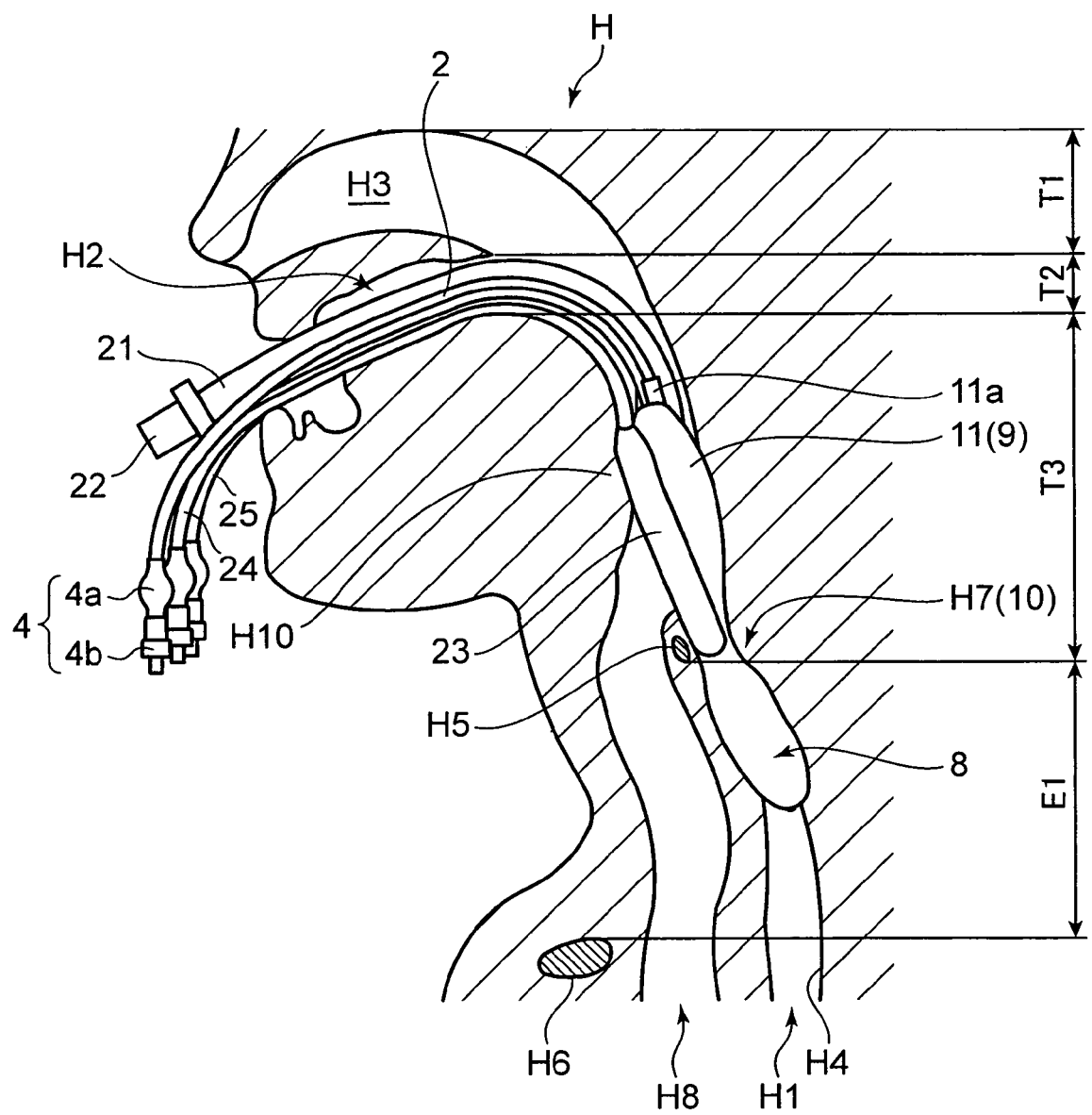
FIG. 10 is a sectional side view showing a state of use of the brain cooling system of FIG. 6.

FIG. 6 is a side view showing the overall configuration of a brain cooling system according to a third embodiment of the invention. FIG. 7 shows the enlarged tip end of the brain cooling system of FIG. 6. FIG. 7A is a plane view and FIG. 7B is a bottom view. FIG. 8 is a cross section taken on line VIII-VIII of FIG. 7. FIG. 9 is a cross section taken on line IX-IX of FIG. 7. FIG. 10 is a sectional side view showing a state of use of the brain cooling system of FIG. 6.

Referring to the respective drawings, a brain cooling system 18 (hereinafter, referred to as the cooling system 18) is formed by combining a pharyngeal mask (airway maintaining member) 19 that allows a gas passage into the trachea H8 while blocking a gas passage into the esophagus H1 of the patient H, and a cooling device 20 that cools the esophagus H1 and the pharyngeal region T of the patient H.

To be more concrete, the pharyngeal region mask 19 includes a tube main body 21 formed in an almost circular arc shape, a connector 22 attached to the base end of the tube main body 21, a pharyngeal cuff 23 externally attached to the tip end of the tube main body 21, a coupling tube 24 extending from the base end of the pharyngeal cuff 23, and the port 4 connected to the base end of the coupling tube 24.

The tube main body 21 is a tubular member made of synthetic resin having flexibility, such as flexible polyvinyl chloride, and provided with a lumen 21a. The tip end of the tube main body 21 is an inclined end face 21b that inclines toward the base end as it is headed toward the center of the circular arc shape.

The connector 22 is a tubular member made of synthetic resin relatively having high rigidity, such as polyethylene, and it is press-inserted into the lumen 21a of the tube main body 21. By connecting an unillustrated artificial respirator to the connector 22, it is possible to supply oxygen into the trachea H8 via the lumen 21a of the tube main body 21.

The pharyngeal cuff 23 is made of a material having flexibility, such as silicone resin, and joined to the tip end of the tube main body 21 along the entire circumference in a posture inclined along the inclined end face 21b of the tube main body 21. The pharyngeal cuff 23 is made hollow for storing a fluid inside and is shaped like an inner tube as a whole.

An attachment cylinder 23a protruding toward the base end is formed in the base end of the pharyngeal cuff 23. The attachment cylinder 23a is joined in a state where the coupling tube 24 is inserted therein. Accordingly, not only is it possible to inflate the pharyngeal cuff 23 via the coupling tube 24 by introducing air from the port 4, but it is also possible to deflate the pharyngeal cuff 23 by discharging air inside the pharyngeal cuff 23 from the port 4.

The pharyngeal mask 19 configured in this manner is used as follows.

As is shown in FIG. 10, the tube main body 21 is inserted into the patient H orally until the tip end of the pharyngeal cuff 23 reaches the branching portion of the esophagus H1 and the trachea H8. Subsequently, the pharyngeal cuff 23 is inflated by introducing air from the port 4.

The inflated pharyngeal cuff 23 comes into close contact with a region in the vicinity of the inlet of the esophagus H1 at the tip end thereof and at the same time it comes into close contact with a region in the vicinity of the pharyngeal palate H10 (see FIG. 5A) at the base end thereof. Consequently, the pharyngeal cuff 23 comes into contact with the trachea H8 along the rim of the opening thereof. Accordingly, a gas, such as oxygen, introduced from the artificial respirator via the connector 22 is guided into the trachea H8 by passing the lumen 21a of the tube main body 21. The airway of the patient H is thus maintained.

Meanwhile, because the cooling device 20 is of almost the same configuration as the cooling device 5 of the second embodiment described above, differences and an assembled state to the pharyngeal mask 19 will be chiefly described hereinafter.

Referring to FIG. 6 through FIG. 10, the cooling device 20 is configured in such a manner that the U-shaped portion 9 is joined to the top surface of the pharyngeal cuff 23. In other words, the U-shaped portion 9 is joined to the pharyngeal cuff 23 while sandwiching the tube main body 21 of the pharyngeal mask 19 between the respective leg portions 11 from the both sides.

Hence, different from the cooling device 5 of the second embodiment in which the crotch portion 12 is provided with the tube 2, the tube 2 of the cooling device 20 extends to the tip end of the bale-shaped portion 8 by penetrating through one of the leg portions 11 so as to avoid the tube main body 21.

In addition, because the U-shaped portion 9 of this embodiment is of a planar shape almost same as the pharyngeal cuff 23, when inserted into the patient H, it is placed in the vicinity of the pharyngeal palate H10 of the patient H, that is, at the hypopharynx T3 (the respective leg portions 11 are made shorter than the counterparts in the second embodiment described above).

Further, while the U-shaped portion 9 is joined to the top surface of the pharyngeal cuff 23, the bale-shaped portion 8 is placed so as to extend from the tip end of the pharyngeal cuff 23 further to a region on the tip end side. Accordingly, in a case where the airway of the patient H is maintained with the pharyngeal cuff 23, the bale-shaped portion 8 is placed in the esophagus H1 of the patient H as is shown in FIG. 10.

In addition, in this embodiment, the discharge tubes 7 provided to the respective leg portions 11 are linked somewhere in midstream to form a merged tube 25. Hence, in comparison with the cooling device 5 of the embodiment described above in which two discharge tubes 7 are introduced to the outside of the body of the patient H, it is possible to make the portion to be inserted into the patient H smaller in volume.

The merged tube 25 and the tube 2 are joined to the both right and left side surfaces of the tube main body 21. Accordingly, because it is possible to insert the tube main body 21, the merged tube 25, and the tube 2 into the patient H at the same time, the operation becomes easier than in a case where the tubes 2, 21, and 25 are inserted separately.

Hereinafter, a method of use of the cooling system 18 will be described.

Initially, the tube main body 21 is inserted into the patient H orally while the pharyngeal cuff 23 and the cuff 6 are deflated. The airway of the patient H is then maintained by inflating the pharyngeal cuff 23 as described above. In this state, the bale-shaped portion 8 is placed in the esophagus H1 of the patient H and the U-shaped portion 9 is placed at the hypopharynx T3.

Subsequently, the cuff 6 is inflated by infusing the cooling agent therein from the port 4 of the tube 2, which brings the bale-shaped portion 8 into close contact with the inner wall H4 of the esophagus H1 and the U-shaped portion 9 with the hypopharynx T3. Accordingly, the inner wall H4 of the esophagus H1 and the pharyngeal region T are cooled by drawing heat from the inner wall H4 and the pharyngeal region T with the cooling agent infused into the cuff 6.

When a specific cooling time has passed, the cuff 6 and the pharyngeal cuff 23 are pulled out from the patient H by pulling out the tube main body 21 after the cuff 6 and the pharyngeal cuff 23 are deflated by discharging the cooling agent from the port 4 of the tube 25.

As has been described, according to the cooling system 18, because the airway of the patient H can be maintained with the pharyngeal mask 19, it is possible to concurrently practice the cardiac arrest resuscitation treatment, such as artificial respiration, and the hypothermic treatment by cooling the brain.

Also, according to the cooling system 18, because the esophagus H1 of the patient H can be blocked with the bale-shaped portion 8 while the airway of the patient H is maintained with the pharyngeal mask 19, not only is it possible to suppress oxygen or the like supplied from the artificial respirator from erroneously flowing into the esophagus H2, but it is also possible to prevent reflux (vomiting) of the content (gastrointestinal fluid) in the stomach of the patient H.

Further, because the U-shaped portion 9 is attached to the pharyngeal cuff 23 in the cooling system 18, by inflating the pharyngeal cuff 23 and the U-shaped portion 9 (cuff 6), it is possible to close the opening of the trachea H8 hermetically by pressures from the both of the pharyngeal cuff 23 and the U-shaped portion 9. Hence, in comparison with a case where the opening of the trachea H8 is blocked using the pharyngeal cuff 23 alone, it is possible to increase the degree of hermetic closing of the trachea H8, which makes it possible to prevent oxygen or the like supplied from the artificial respirator from leaking to the outside of the trachea H8 (toward the pharyngeal region T) in a more reliable manner.

The cooling system 18 has been described in the configuration in which the pharyngeal mask 19 and the cooling device 20 are combined into a single unit. However, the pharyngeal mask 19 and the cooling device 20 can be formed separately. In this case, by inserting the cooling device 20 into the patient H along the tube main body 21 of the pharyngeal mask 19 while the pharyngeal mask 19 is inserted into the patient H, it is possible to cool the esophagus H1 and the pharyngeal region T of the patient H. In this case, the cuff 6 of the cooling device 20 has to be inserted before air is infused into the pharyngeal cuff 23.

In the cooling system 18, it is configured in such a manner that the cooling device 20 is assembled to the pharyngeal mask 19. However, the cooling device 1 of the first embodiment above can be assembled to the pharyngeal mask 19 as well. In this case, it is possible to cool the inner wall H4 of the esophagus H1 of the patient H with the cooling device 1 while the airway of the patient H is maintained with the pharyngeal mask 19.

In the third embodiment, the pharyngeal mask 19 was described as an example of the airway maintaining member. However, as the airway maintaining member, a nasal airway to be inserted transnasally, an esophageal obturator airway, and the like can be adopted as well.

In the cooling system 18, the cooling device 20 is assembled to the pharyngeal mask 19 for maintaining airway. However, the configuration to maintain the airway may be additionally provided to the cooling device itself.

Figure 11:
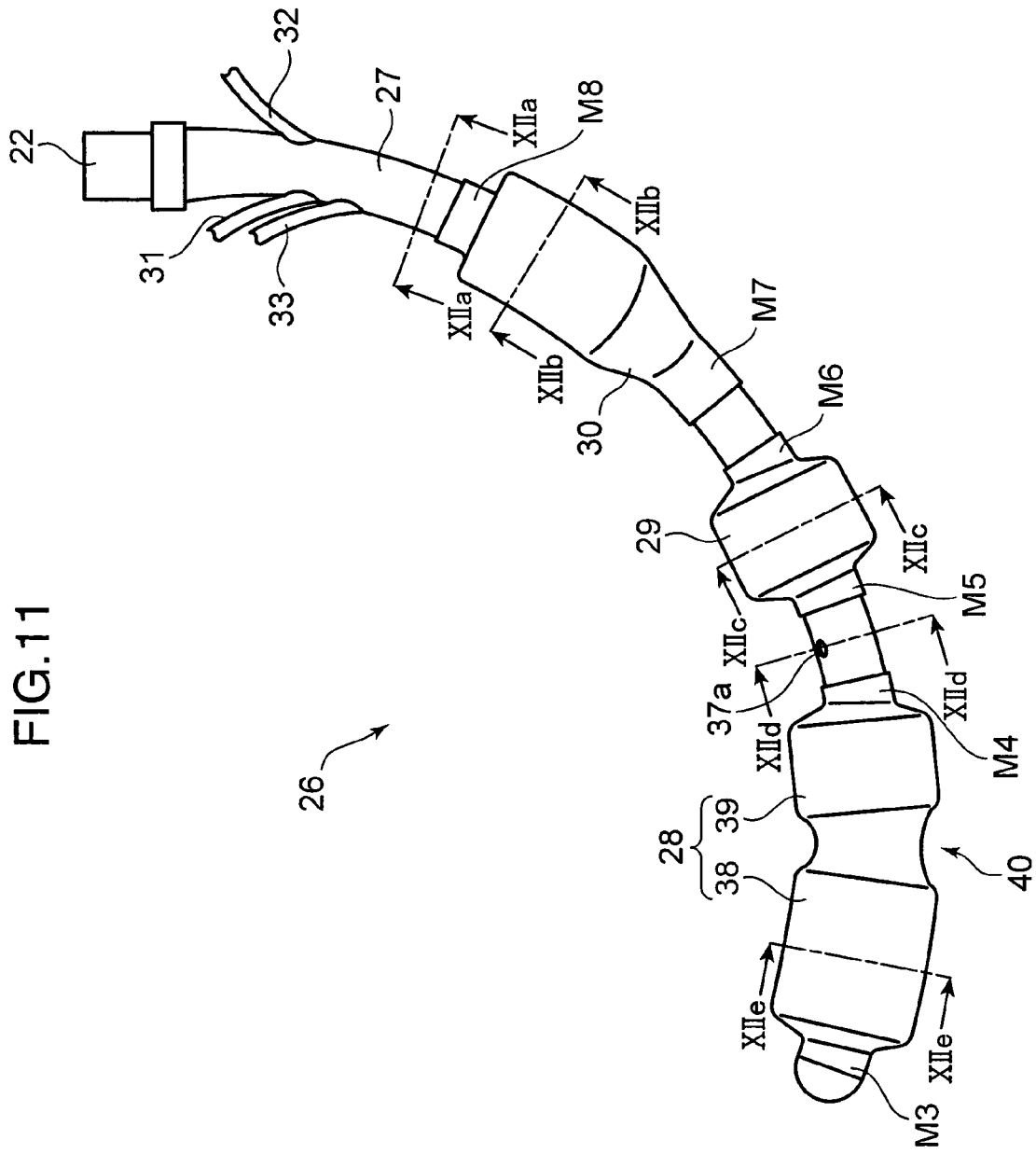
FIG. 11 is a side view showing the overall configuration of a cooling device according to a fourth embodiment of the invention.
Figure 12A:
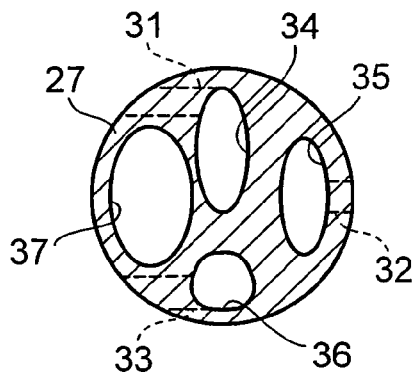
FIG. 12A is a cross section taken on line XIIa-XIIa of FIG. 11.
Figure 12B:
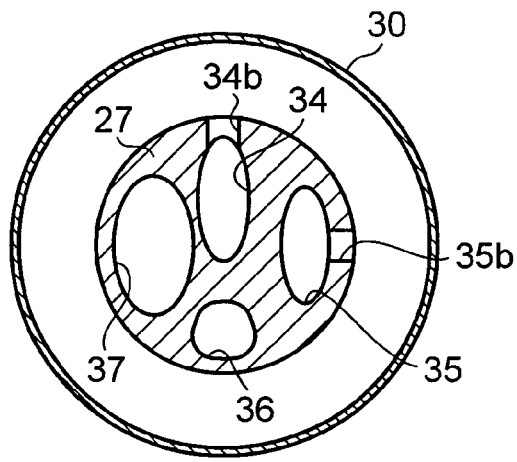
FIG. 12B is a cross section taken on line XIIb-XIIb of FIG. 11.
Figure 12C:
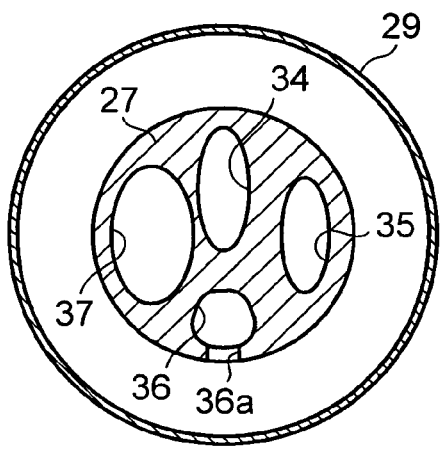
FIG. 12C is a cross section taken on line XIIc-XIIc of FIG. 11.
Figure 12D:
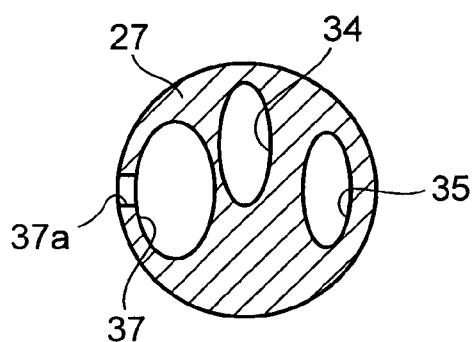
FIG. 12D is a cross section taken on line XIId-XIId of FIG. 11.
Figure 12E:
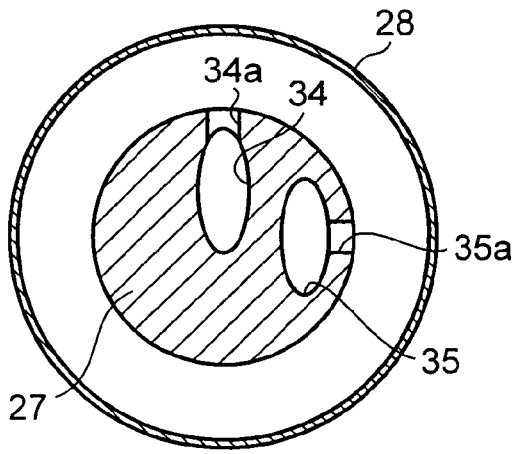
FIG. 12E is a cross section taken on line XIIe-XIIe of FIG. 11.
Figure 13:
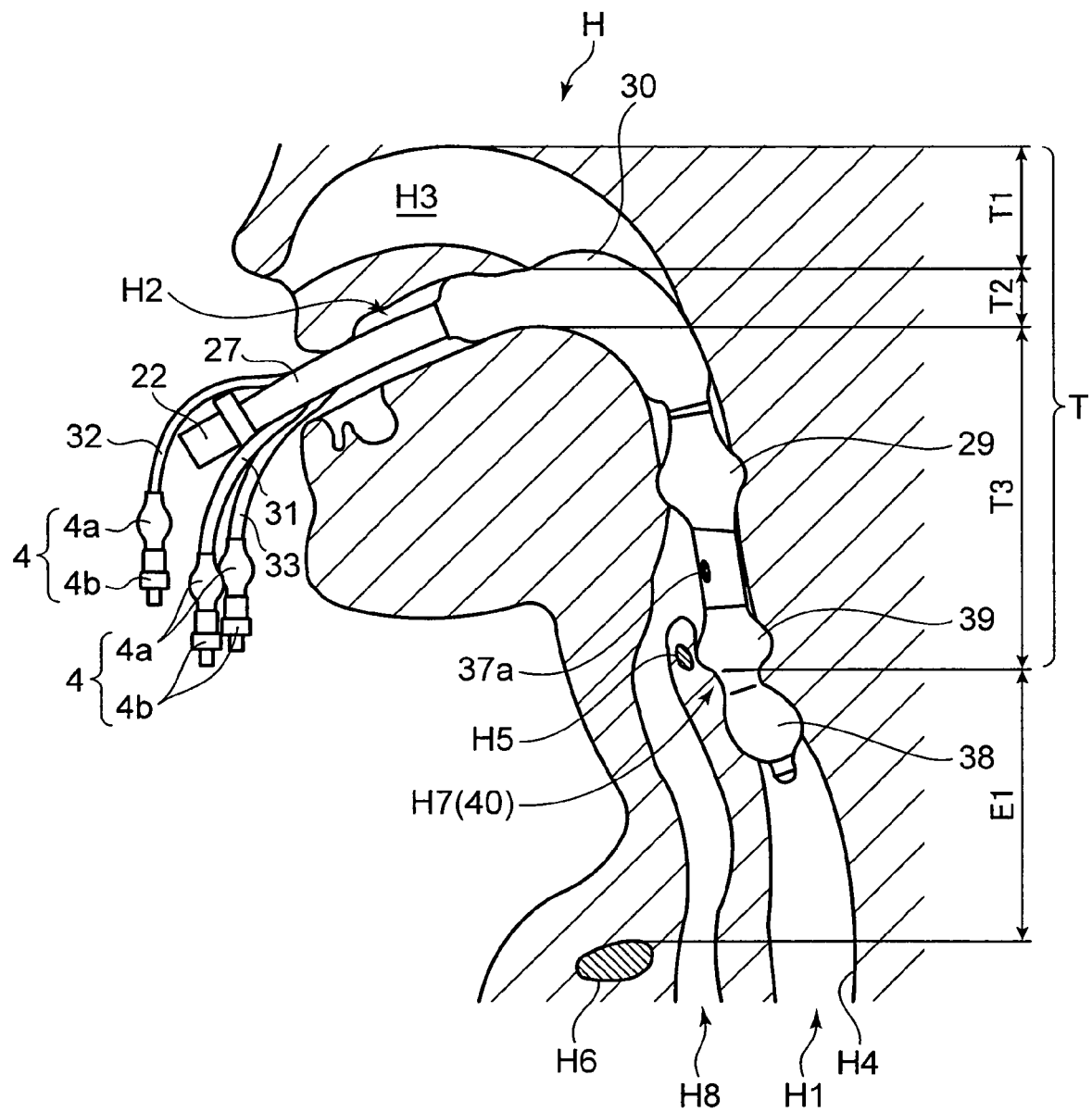
FIG. 13 is a sectional side view showing a state where the cooling device of FIG. 11 is inserted into the patient.

FIG. 11 is a side view showing the overall configuration of a cooling device according to a fourth embodiment of the invention. FIG. 12A is a cross section taken on line XIIa-XIIa of FIG. 11. FIG. 12B is a cross section taken on line XIIb-XIIb of FIG. 11. FIG. 12C is a cross section taken on line XIIc-XIIc of FIG. 11. FIG. 12D is a cross section taken on line XIId-XIId of FIG. 11. FIG. 12E is a cross section taken on line XIIe-XIIe of FIG. 11. FIG. 13 is a sectional side view showing a state where the cooling device of FIG. 11 is inserted into the patient.

Referring to the respective views, a brain cooling device 26 (hereinafter, referred to as the cooling device 26) includes a tube (infusion and discharge means) 27, a cooling cuff (storage portion) 28 provided to the tube 27, a blocking cuff 29, a pharyngeal cuff 30, and the connector 22 press-inserted into the base end of the tube 27.

The tube 27 includes an introduction tube 31 connected to the base end thereof, a discharge tube 32, a gas tube 33, and the port 4 coupled to each of the tubes 31 through 33.

The tube 27 is provided with four lumens along the axial line direction, including a cooling agent introduction hole 34, a cooling agent discharge hole 35, a gas hole 36, and an airway maintaining hole 37.

The cooling agent introduction hole 34 is formed in a range from the base end to which the introduction tube 31 is joined to the tip end corresponding to the position at which the cooling cuff 28 is placed. As is shown in FIG. 12E, the cooling agent introduction hole 34 is open to the side of the tube 27 at the tip end by a side hole 34a that penetrates through the tube 27, and as is shown in FIG. 12B, it is open to the side of the tube 27 in midstream by a side hole 34b that penetrates through the tube 27.

Likewise, the cooling agent discharge hole 35 is formed in a range from the base end to which the discharge tube 32 is joined to the tip end corresponding to the position at which the cooling cuff 28 is placed. As is shown in FIG. 12E, the cooling agent discharge hole 35 is open to the side of the tube 27 at the tip end by a side hole 35a that penetrates through the tube 27, and as is shown in FIG. 12B, it is open to the side of the tube 27 in midstream by a side hole 35b that penetrates through the tube 27.

The gas hole 36 is provided in a range from the base end to which the gas tube 33 is joined to the tip end corresponding to the position at which the blocking cuff 29 is placed. As is shown in FIG. 12C, the gas hole 36 is open to the side of the tube 27 at the tip end by a side hole 36a that penetrates through the tube 27.

The airway maintaining hole 37 is provided in a range from the base end of the tube 27 into which the connector 22 is press-inserted to the tip end between the cooling cuff 28 and the blocking cuff 29. As is shown in FIG. 12D, the airway maintaining hole 37 is open to the side of the tube 27 at the tip end by a side hole 37a that penetrates through the tube 27.

The cooling cuff 28 is formed in the shape of a bag by externally attaching a member made of silicone resin or the like and formed in a circular cylindrical shape to the tube 27 so as to cover the respective side holes 34a and 35a and then joining the both ends thereof to the outer peripheral surface of the tube 27 along the entire circumference at joint positions M3 and M4 on the tip end side and the base end side of the side holes 34a and 35a, respectively. The cooling agent introduced from the introduction tube 31 is stored between the cooling cuff 28 and the tube 27 thus joined to each other, while the cooling agent introduced between the cooling cuff 28 and the tube 27 is discharged via the discharge tube 32.

In addition, the cooling cuff 28 includes a esophagus-placed portion 38 to be placed in the esophagus H1 of the patient H, a pharynx-placed portion 39 to be placed at the hypopharynx T3 of the patient H, and a recess portion 40 formed between these portions 38 and 39 to have a cross section in an inflated state smaller than those of these portions 38 and 39, all of which are combined into a single unit.

The blocking cuff 29 is formed in the shape of a bag by externally attaching a member made of silicone resin or the like and formed in a circular cylindrical shape to the tube 27 so as to cover the side hole 36a and then joining the both ends thereof to the outer peripheral surface of the tube 27 along the entire circumference at joint positions M5 and M6 on the tip end side and on the base end side of the side hole 36a, respectively. A fluid is stored between the blocking cuff 29 and the tube 27 thus joined to each other via the gas tube 33, while the fluid stored between the blocking cuff 29 and the tube 27 is discharged via the gas tube 33.

As is shown in FIG. 13, the blocking cuff 29 is laid out in the esophagus-placed portion 38 so as to be placed at the hypopharynx T3 of the patient H when the tube 27 is inserted into the patient H orally while the esophagus-placed portion 38 is placed in the esophagus H1 of the patient H.

The pharyngeal cuff 30 is formed in the shape of a bag by externally attaching a member made of silicone resin or the like and formed in a circular cylindrical shape to the tube 27 so as to cover the respective side holes 34b and 35b and then joining the both ends thereof to the outer peripheral surface of the tube 27 along the entire circumference at joint positions M7 and M8 on the tip end side and the base end side of the side holes 34b and 35b, respectively. The cooling agent introduced from the introduction tube 31 is stored between the pharyngeal cuff 30 and the tube 27 thus joined to each other, while the cooling agent introduced between the pharyngeal cuff 30 and the tube 27 is discharged via the discharge tube 32.

Also, as is shown in FIG. 13, the pharyngeal cuff 30 is laid out in the esophagus-placed portion 38 so that it is placed in a range from the hypopharynx T3 to the mouth cavity H2 through the oropharynx T2 of the patient H in a case where the tube 27 is inserted into the patient H orally and the esophagus-placed portion 38 is placed in the esophagus H1 of the patient H.

Hereinafter, a method of use of the cooling device 26 will be described.

Initially, air inside the blocking cuff 29 and the cooling agent inside the cooling cuff 28 and the pharyngeal cuff 30 are discharged using the ports 4 connected to the discharge tube 32 and the gas tube 33 so as to deflate these cuffs 28 through 30.

In this state, the tube 27 is inserted into the patient H orally from the tip end, and as is shown in FIG. 13, the esophagus-placed portion 38 of the cooling cuff 28 is placed in the esophagus H1 of the patient H. Accordingly, the recess portion 40 of the cooling cuff 28 is placed at the narrow segment H7 of the patient H, and the blocking cuff 29 is placed in the vicinity of the pharyngeal palate H10 of the patient H (see FIG. 5A). Further, the pharyngeal cuff 30 is placed in a range from the hypopharynx T3 to the mouth cavity H2 of the patient H through the oropharynx T2.

Subsequently, the cooling cuff 28, the blocking cuff 29, and the pharyngeal cuff 30 are inflated by infusing the cooling agent from the port 4 connected to the introduction tube 31 and infusing air form the port 4 connected to the gas tube 33. Accordingly, the blocking cuff 29 comes into close contact with the hypopharynx T3 of the patient H and the cooling cuff 28 with the inner wall H4 of the esophagus H1 of the patient. However, because the airway maintaining hole 37 is open via the side hole 37a between these cuffs 28 and 30, oxygen from the artificial respirator connected to the connector 22 is supplied inside the trachea of the patient H.

Concurrently, the oropharynx T2 and the hypopharynx T3 as well as the inner wall H4 of the esophagus H1 of the patient H are cooled with the cooling cuff 28 and the pharyngeal cuff 30 into which the cooling agent has been infused.

The tube 27 can be pulled out to the outside of the body after these cuffs 28 through 30 are deflated by discharging the cooling agent and air inside the cooling cuff 28, the blocking cuff 29, and the pharyngeal cuff 30.

As has been described, according to the cooling device 26, because the airway of the patient H can be maintained with the tube 27, it is possible to concurrently practice the cardiac arrest resuscitation treatment, such as artificial respiration, and the hypothermic treatment by cooling the brain.

This embodiment described the method for infusing air into the blocking cuff 29. However, the cooling agent may be infused into the blocking cuff 29.

Also, this embodiment described a case where the tube 27 is inserted orally. However, it is possible to insert the tube 27 transnasally.

More specifically, the invention provides a brain cooling device, characterized by including: a first storage portion capable of storing therein a cooled fluid and placeable in an esophagus of an organism when inserted orally or transnasally; a second storage portion to be placed at a pharyngeal region of the organism while the first storage portion is placed in the esophagus of the organism and cable of storing therein the cooled fluid; and infusion and discharge means provided so as to extend from the first and second storage portions for fusing the fluid into the first and second storage portions placed in the organism from outside a body of the organism and discharging the fluid from the first and second storage portions, wherein the first and second storage portions have flexibility to inflate or deflate in response to infusion or discharge of the fluid and are configured in such a manner that when the fluid is infused therein while placed in the organism, the first storage portion that has been inflated comes into close contact with an inner wall of the esophagus and the second portion that has been inflated comes into close contact with the pharyngeal region.

According to the invention, by infusing the fluid into the storage portion placed in the esophagus, the storage portion can be brought into close contact with the inner wall of the esophagus. It is thus possible to cool the inner wall of the esophagus with the cooled fluid inside the storage portion. Because blood vessels (carotid arteries) that supply blood to the brain are concentrated in the vicinity of the esophagus, cooling these blood vessels with the storage portion makes it possible to cool the brain by cooling the blood flowing in these blood vessels.

As has been described, according to the invention, not only can the brain be cooled in a short time because the blood vessels in a relatively close distance from the brain are cooled from inside the body (esophagus), but also the brain can be cooled sufficiently to the subcortical tissue because the brain is cooled via the blood.

Also, according to the invention, because the brain is cooled by cooling the inner wall of the esophagus alone, in comparison with a case where the whole body is cooled, it is possible to suppress a drop in temperature of the whole body, which can reduce concerns about the cooling timing.

Further, according to the invention, by infusing the fluid into the second storage portion placed at the pharyngeal region (a region closer to the mouth or the nose than to the esophagus: indicated by a capital T in FIG. 5B), the second storage portion can be brought into close contact with the pharyngeal region. It is thus possible to cool the pharyngeal region with the cooled fluid inside the second storage portion. Also, as with the esophagus, because blood vessels (carotid arteries) that supply blood to the brain are concentrated in the vicinity of the pharyngeal region, too, cooling these blood vessels with the second storage portion makes it possible to cool the brain by cooling the blood flowing in these blood vessels.

Hence, according to this configuration, combined with the cooling of the inner wall of the esophagus, it is possible to cool the brain more effectively.

In the brain cooling device described above, it is preferable that the infusion and discharge means has rigidity larger than rigidity of at least the storage portion to enable an operation to push the storage portion inserted orally or transnasally further into the esophagus.

According to this configuration, because the storage portion can be pushed further into the esophagus by the infusion and discharge means, it is possible to eliminate a work to insert a guide wire or the like before insertion of the storage portion.

Although it is not intended to limit the shape of the infusion and discharge means, it is preferable that the infusion and discharge means is formed to penetrate through the storage portion from a tip end of the storage portion being placed in a deeper portion of the esophagus to a base end of the storage portion on an opposite side.

According to this configuration, because it is possible to render elasticity (rigidity) to the storage portion itself along the insertion direction when the storage portion is inserted orally or transnasally, it is possible to introduce the storage portion into the esophagus in a more reliable manner.

The function of infusing the fluid into the storage portion and the function of discharging the fluid inside the storage portion may be provided to common infusion and discharge means. However, it is preferable that the infusion and discharge means separately includes infusion means for infusing the fluid into the storage portion and discharge means for discharging the fluid inside the storage portion, and that the infusion means infuses the fluid into the storage portion to be placed in a deeper portion of the esophagus on a tip end side thereof and the discharge means discharges the fluid inside the storage portion from a base end on a side opposite to the tip end.

According to this configuration, because the fluid can be infused from the lower side (the tip end side) of the storage portion placed inside the esophagus of the organism while discharging the fluid from the upper portion (the base end side) of the storage portion, it is possible to allow the fluid that has absorbed heat of the organism inside the storage portion to flow inside the storage portion along a direction of convection, so that the fluid having heat is discharged actively from the storage portion.

Hence, according to this configuration, because the efficiency of heat exchange between the organism and the storage portion can be enhanced, it is possible to cool the brain more effectively.

Although it is not intended to exclude the configuration to form the storage portion and the second storage portion separately, it is preferable that the storage portion and the second storage portion are combined into a single unit, and a recess portion whose sectional area in an inflated state is made smaller than sectional areas of other portions is formed at a boundary of the storage portion and the second storage portion.

According to this configuration, when both the storage portion and the second portion are inflated while the storage portion is placed in the esophagus and the second storage portion at the pharyngeal region, it is possible to suppress application of an excessive load on the narrow segment (indicated by reference numeral H7 in FIG. 5) at the boundary of the pharyngeal region and the esophagus of the organism.

In the brain cooling device described above, it is preferable that the infusion and discharge means separately includes infusion means for infusing the fluid into the storage portion and discharge means for discharging the fluid inside the storage portion, and that the infusion means infuses the fluid into the storage portion to be placed in a deeper portion of the esophagus on a tip end side thereof and the discharge means discharges the fluid inside the storage portion and the second storage portion from a base end of the second storage portion on a side opposite to the tip end.

According to this configuration, because the fluid can be infused from the lower portion (on the tip end side) of the storage portion placed in the esophagus of the organism while discharging the fluid from the upper portion (the base end side) of the second storage portion disposed above the storage portion, it is possible to allow the fluid that has absorbed heat of the organism inside the storage portion and the second storage portion to flow along a direction of convection, so that the fluid having heat is discharged actively.

Hence, according to this configuration, because the efficiency of heat exchange between the organism and the storage portion and the second storage portion can be enhanced, it is possible to cool the brain more effectively by increasing the cooling efficiency of the inner wall of the esophagus and the pharyngeal region.

Further, it is preferable that the infusion and discharge means is formed of a tubular member provided with a lumen for maintaining an airway of the organism when inserted orally or transnasally, and that the tubular member is provided with a communication hole that communicates with an interior of the storage portion separately from the lumen.

According to this configuration, because the airway of the organism can be maintained with the tubular member, it is possible to concurrently practice the cardiac arrest resuscitation treatment, such as artificial respiration, and the hypothermic treatment by cooling the brain.

To be more concrete, the storage portion is formed by joining a flexible tube externally attached to the tubular member along a longitudinal direction thereof to an outer peripheral surface of the tubular member along an entire circumference at two points in the longitudinal direction, and the tubular member is provided with a side hole that is open between the respective joint portions and coupled to the communication hole, so that the fluid is stored between the flexible tube and the tubular member via the communication hole and the side hole, or the fluid stored between the flexible tube and the tubular member is discharged via the communication hole and the side hole.

According to this configuration, after the tubular member is inserted into the esophagus, by infusing the fluid via the communication hole of the tubular member to inflate the storage portion outwardly in the radial direction of the tubular member, it is possible to bring the storage portion into close contact with the inner wall of the esophagus.

In addition, the invention provides a brain cooling system, including the brain cooling device described above, and an airway maintaining member capable of maintaining an airway of the organism when inserted orally or transnasally, to which the brain cooling device is attached.

According to the brain cooling system of the invention, because the airway of the organism can be maintained with the airway maintaining member, it is possible to concurrently practice the cardiac arrest resuscitation treatment, such as artificial respiration, and the hypothermic treatment by cooling the brain.

The phrase, "to which the brain cooling device is attached", means not only that the brain cooling device and the airway maintaining member are combined into a single unit, but also that these components are removable. To be more specific, in a case where the brain cooling system is inserted into the organism orally or transnasally, the airway maintaining member may be inserted into the organism orally or transnasally before insertion of the brain cooling device for introducing the brain cooling device into the esophagus along the airway maintaining member.

Meanwhile, in a case where the brain cooling device and the airway maintaining member are combined into a single unit, an operation to insert the both components into the organism can be carried out at a time, which can enhance the workability.

INDUSTRIAL APPLICABILITY

According to the invention, it is possible to cool the brain sufficiently to the subcortical tissue in a short time.

The invention claimed is:

1. A brain cooling device, comprising:
a first storage portion capable of storing therein a cooled fluid and placeable in an esophagus of an organism when inserted orally or transnasally;
a second storage portion to be placed at a pharyngeal region of the organism while the first storage portion is placed in the esophagus of the organism and capable of storing therein the cooled fluid; and
infusion and discharge means provided so as to extend from the first and second storage portions for infusing the fluid into the first and second storage portions placed in the organism from outside a body of the organism and discharging the fluid from the first and second storage portions, wherein the first and second storage portions have flexibility to inflate or deflate in response to infusion or discharge of the fluid and are configured in such a manner that when the fluid is infused therein while placed in the organism, the first storage portion that has been inflated comes into close contact with an inner wall of the esophagus and the second storage portion that has been inflated comes into close contact with the pharyngeal region, wherein the infusion and discharge means includes an infusion member for infusing the fluid into the first storage portion and a discharge member for discharging the fluid inside the storage portion, and the infusion member infuses the fluid into the first storage portion to be placed in a deeper portion of the esophagus on a tip end side thereof and the discharge member discharges the fluid inside the first storage portion from a base end on a side opposite to the tip end.

2. The brain cooling device according to claim 1, wherein: the infusion and discharge means has rigidity larger than rigidity of at least the first storage portion to enable an operation to push the first storage portion inserted orally or transnasally further into the esophagus.

3. The brain cooling device according to claim 2, wherein: the infusion and discharge means is formed to penetrate through the first storage portion from a tip end of the storage portion being placed in a deeper portion of the esophagus to a base end of the storage portion on an opposite side.

4. A brain cooling device, comprising:
a first storage portion capable of storing therein a cooled fluid and placeable in an esophagus of an organism when inserted orally or transnasally;
a second storage portion to be placed at a pharyngeal region of the organism while the first storage portion is placed in the esophagus of the organism and capable of storing therein the cooled fluid; and
infusion and discharge means provided so as to extend from the first and second storage portions for infusing the fluid into the first and second storage portions placed in the organism from outside a body of the organism and discharging the fluid from the first and second storage portions,
wherein the first and second storage portions have flexibility to inflate or deflate in response to infusion or discharge of the fluid and are configured in such a manner that when the fluid is infused therein while placed in the organism, the first storage portion that has been inflated comes into close contact with an inner wall of the esophagus and the second storage portion that has been inflated comes into close contact with the pharyngeal region, wherein
the first storage portion and the second storage portion are combined into a single unit, and a recess portion whose sectional area in an inflated state is made smaller than sectional areas of other portions is formed at a boundary of the first storage portion and the second storage portion.

5. The brain cooling device according to claim 4, wherein:
the infusion and discharge means includes an infusion member for infusing the fluid into each storage portion and a discharge member for discharging the fluid inside each storage portion; and
the infusion member infuses the fluid into the first storage portion to be placed in a deeper portion of the esophagus on a tip end side thereof and the discharge member discharges the fluid inside the first storage portion and the second storage portion from a base end of the second storage portion on a side opposite to the tip end.

6. A brain cooling, comprising:
a first storage portion capable of storing therein a cooled fluid and placeable in an esophagus of an organism when inserted orally or transnasally;
a second storage portion to be placed at a pharyngeal region of the organism while the first storage portion is placed in the esophagus of the organism and capable of storing therein the cooled fluid; and
infusion and discharge means provided so as to extend from the first and second storage portions for infusing the fluid into the first and second storage portions placed in the organism from outside a body of the organism and discharging the fluid from the first and second storage portions, wherein
the first and second storage portions have flexibility to inflate or deflate in response to infusion or discharge of the fluid and are configured in such a manner that when the fluid is infused therein while placed in the organism, the first storage portion that has been inflated comes into close contact with an inner wall of the esophagus and the second storage portion that has been inflated comes into close contact with the pharyngeal region, wherein:
the infusion and discharge means is formed of a tubular member provided with a lumen for maintaining an airway of the organism when inserted orally or transnasally; and
the tubular member is provided with a communication hole that communicates with an interior of each storage portion separately from the lumen.

7. The brain cooling device according to claim 6, wherein:
the first storage portion is formed by joining a flexible tube externally attached to the tubular member along a longitudinal direction thereof to an outer peripheral surface of the tubular member along an entire circumference at two points in the longitudinal direction, and the tubular member is provided with a side hole that is open between the respective joint portions and coupled to the communication hole, so that the fluid is stored between the flexible tube and the tubular member via the communication hole and the side hole, or the fluid stored between the flexible tube and the tubular member is discharged via the communication hole and the side hole.

8. A brain cooling system, comprising:
the brain cooling device set forth in claim 1; and
an airway maintaining member capable of maintaining an airway of the organism when inserted orally or transnasally, to which the brain cooling device is attached.

* * * * *